(12) United States Patent
Gamliel

(10) Patent No.: US 10,709,843 B2
(45) Date of Patent: Jul. 14, 2020

(54) DEVICE AND METHOD FOR REPETITIVE NEEDLELESS INJECTION

(71) Applicant: KOLORPEN LTD., Afula (IL)

(72) Inventor: Reuven Gamliel, Afula (IL)

(73) Assignee: KOLORPEN LTD., Afula (IL)

( * ) Notice: Subject to any disclaimer, the term of this patent is extended or adjusted under 35 U.S.C. 154(b) by 221 days.

(21) Appl. No.: 15/509,222

(22) PCT Filed: Apr. 7, 2016

(86) PCT No.: PCT/IL2016/050369
§ 371 (c)(1),
(2) Date: Mar. 7, 2017

(87) PCT Pub. No.: WO2016/181377
PCT Pub. Date: Nov. 17, 2016

(65) Prior Publication Data
US 2018/0056004 A1 Mar. 1, 2018

Related U.S. Application Data

(60) Provisional application No. 62/159,285, filed on May 10, 2015.

(51) Int. Cl.
*A61M 5/30* (2006.01)
*A61M 5/32* (2006.01)
(Continued)

(52) U.S. Cl.
CPC ............ *A61M 5/3007* (2013.01); *A61M 5/30* (2013.01); *A61M 5/3286* (2013.01); *A61M 5/46* (2013.01);
(Continued)

(58) Field of Classification Search
CPC ......... A61M 5/3007; A61M 5/30; A61M 5/48
See application file for complete search history.

(56) References Cited

U.S. PATENT DOCUMENTS 5,840,062 A * 11/1998 Gumaste .................. A61M 5/30
604/68
6,610,028 B1    8/2003 Alexandre et al.
(Continued)

FOREIGN PATENT DOCUMENTS

CN    201091718    7/2008
CN    201131985    10/2008
(Continued)

OTHER PUBLICATIONS

Supplementary European Search Report for European Application No. 16 79 2296 dated Jan. 8, 2019.
(Continued)

*Primary Examiner* — Rebecca E Eisenberg
*Assistant Examiner* — Tasnim Mehjabin Ahmed
(74) *Attorney, Agent, or Firm* — Pearl Cohen Zedek Latzer Baratz LLP

(57) ABSTRACT

A device for repetitive needleless injection of a liquid into a surface includes a handheld unit that includes at least a cell that is fillable with the liquid. A propulsion mechanism is configured to apply a sequence of pressure pulses to the liquid. Each pulse ejects a micro jet of the liquid from the cell via an orifice between the cell and the exterior of the handheld unit with a velocity that is sufficient to enable the micro-jet to penetrate into the surface. A reservoir is connected to the cell by a conduit to enable the liquid to flow from the reservoir to the cell to replace the liquid that is ejected in the micro-jet. A controller is configured to operate the propulsion mechanism repeatedly so as to eject the sequence of the micro-jets.

15 Claims, 8 Drawing Sheets

(51) Int. Cl.
*A61M 5/31* (2006.01)
*A61M 5/46* (2006.01)
*A61M 5/20* (2006.01)

(52) U.S. Cl.
CPC ..... *A61M 5/204* (2013.01); *A61M 2005/3128* (2013.01); *A61M 2205/50* (2013.01)

(56) References Cited

U.S. PATENT DOCUMENTS

| | | | |
|---|---|---|---|
| 7,261,702 | B1 | 8/2007 | Alexandre et al. |
| 2003/0065294 | A1 | 4/2003 | Pickup et al. |
| 2003/0083611 | A1 | 5/2003 | Angel et al. |
| 2004/0055662 | A1 | 3/2004 | Neracher |
| 2004/0158195 | A1 | 8/2004 | Sibert et al. |
| 2005/0154369 | A1 | 7/2005 | Broullette et al. |
| 2005/0187516 | A1 | 8/2005 | Neracher |
| 2006/0258986 | A1* | 11/2006 | Hunter ............... A61D 7/00 604/164.01 |
| 2007/0043320 | A1 | 2/2007 | Kenany |
| 2007/0049864 | A1 | 3/2007 | Hansen |
| 2007/0167906 | A1 | 7/2007 | Alexandre et al. |
| 2009/0030367 | A1 | 1/2009 | Arora et al. |
| 2009/0043320 | A1 | 2/2009 | Seto et al. |
| 2009/0082753 | A1 | 3/2009 | Dutcher et al. |
| 2012/0059314 | A1* | 3/2012 | Eichhorst ............... A61M 5/204 604/68 |
| 2012/1017913 | | 7/2012 | Garitano et al. |

FOREIGN PATENT DOCUMENTS

| | | |
|---|---|---|
| CN | 201361320 | 2/2009 |
| CN | 201399128 | 2/2010 |
| CN | 101690834 | 4/2010 |
| CN | 202620427 | 12/2012 |
| JP | 2004008244 | 1/2004 |
| WO | WO 00/64514 | 11/2000 |
| WO | WO 2004/101025 | 11/2004 |
| WO | WO 2007/058966 | 5/2007 |
| WO | WO 2007/149514 | 12/2007 |
| WO | WO 2008/001377 | 1/2008 |
| WO | WO 2011/004290 | 1/2011 |

OTHER PUBLICATIONS

"Transdermal Patches, Microneedles & Needle-free Injection: Manufacturing Lines Roll As Concepts Become Products" ONdrug Delivery Mar./Apr. 2013 Issue No. 40 ISSN-2049-145X. pp. 1-36.

Wendell, Dawn Marie. *Controllable needle-free injection: "Development and verification of a novel device"*. Diss. Massachusetts Institute of Technology, 2006. pp. 1-45.

Han, Tae-hee, Jung-moo Hah, and Jack J. Yoh. "Drug injection into fat tissue with a laser based microjet injector." *Journal of Applied Physics* 109.9 (2011): 093105. pp. 1-3.

Park, Mi-ae, et al. "Er: YAG laser pulse for small-dose splashback-free microjet transdermal drug delivery." *Optics letters* 37.18 (2012):3894-3896. pp. 1-3.

Stachowiak, Jeanne C., et al. "Piezoelectric control of needle-free transdermal drug delivery." *Journal of Controlled Release* 124.1 (2007): 88-97. pp. 1-10.

Stachowiak, Jeanne C., et al. "Dynamic control of needle-free jet injection." *Journal of Controlled Release* 135.2 (2009): 104-112. pp. 1-9.

Arora, Anubhav, et al. "Needle-free delivery of macromolecules across the skin by nanoliter-volume pulsed microjets." *Proceedings of the National Academy of Sciences* 104.11 (2007): 4255-4260. pp. 1-6.

International Search Report for PCT Application No. PCT/IL2016/050369 dated Jul. 14, 2016.

\* cited by examiner

DEVICE AND METHOD FOR REPETITIVE NEEDLELESS INJECTION

CROSS-REFERENCE TO RELATED APPLICATIONS

This application is a National Phase Application of PCT International Application No. PCT/IL2016/050369, International Filing Date Apr. 7, 2016, claiming the benefit of U.S. Provisional Patent Application No. 62/159,285, filed on May 10, 2015, all of which are hereby incorporated by reference.

FIELD OF THE INVENTION

The present invention relates to injection. More particularly, the present invention relates to a device and method for repetitive needleless injection.

BACKGROUND OF THE INVENTION

Drugs, vaccinations, and other medical materials that are to be delivered to tissue that is covered by skin are typically injected using a hypodermic needle. Similarly, tattoos and permanent makeup are also typically applied using needles that penetrate the skin surface.

Although the use of needles for transcutaneous or subsurface delivery is well established, being very robust and reliable, there are some disadvantages to the use of needles. For example, reuse of needles may be a common practice in regions or circumstances where an adequate supply of needles cannot be relied upon. Such reuse of a needle after inadequate sterilization could lead to infection or spread of disease agents from person to person. Some people are frightened by the sight of the needle and by the realization that the needle is to penetrate their skin. Insertion of the needle is an invasive procedure which could be painful, cause bleeding, or otherwise traumatize tissue to some extent. In some cases, momentary inattention to an exposed needle may result in accidental pricking of medical personnel or of bystanders, possibly resulting in injury or infection.

Needleless transcutaneous or subsurface delivery may require a smaller amount of the delivered liquid than delivery via a needle. Reducing the amount of the delivered liquid may reduce the probability of skin irritation or an allergic reaction.

SUMMARY OF THE INVENTION

There is thus provided, in accordance with an embodiment of the present invention, a device for repetitive needleless injection of a liquid into a surface, the device including: a handheld unit that includes at least a cell that is fillable with the liquid, and a propulsion mechanism configured to apply a sequence of pressure pulses to the liquid, each pulse of the sequence of pressure pulses to eject a micro-jet of the liquid from the cell via an orifice between the cell and the exterior of the handheld unit with a velocity that is sufficient to enable the micro-jet to penetrate into the surface; a reservoir that is connected to the cell by a conduit to enable the liquid to flow from the reservoir to the cell to replace the liquid that is ejected in the micro-jet; and a controller that is configured to operate the propulsion mechanism repeatedly so as to eject a sequence of the micro-jets.

Furthermore, in accordance with an embodiment of the present invention, the orifice is separated from the cell by a unidirectional valve that is configured to enable flow of the liquid from the cell to the orifice and to prevent inflow from the orifice to the cell.

Furthermore, in accordance with an embodiment of the present invention, the unidirectional valve includes a stopper that is separable from an aperture.

Furthermore, in accordance with an embodiment of the present invention, a connection of the conduit to the cell includes a unidirectional valve to enable the liquid to flow from the conduit to the cell and to prevent backflow of liquid from the cell to the conduit.

Furthermore, in accordance with an embodiment of the present invention, the propulsion mechanism includes an impulse generator configured to displace an actuation surface to generate the pulse and a plunger configured to move linearly to transmit the pulse to the cell.

Furthermore, in accordance with an embodiment of the present invention, the impulse generator includes a piezoelectric crystal.

Furthermore, in accordance with an embodiment of the present invention, the impulse generator includes a mechanical amplifier.

Furthermore, in accordance with an embodiment of the present invention, the plunger is bonded to the actuation surface.

Furthermore, in accordance with an embodiment of the present invention, the plunger is provided with a retraction mechanism that is configured to retract the plunger after application of the pulse by the actuation surface.

Furthermore, in accordance with an embodiment of the present invention, the retraction mechanism includes a spring.

Furthermore, in accordance with an embodiment of the present invention, the impulse generator is configured to expand to compress a propulsion resilient element and to contract to enable expansion of the propulsion resilient element to distally propel the plunger.

Furthermore, in accordance with an embodiment of the present invention, the controller is configured to control operation of the propulsion mechanism so as to control one or both of an amplitude of the pulse and a rise time of the pulse.

Furthermore, in accordance with an embodiment of the present invention, the controller is configured to control the one or both of an amplitude of the pulse and a rise time of the pulse in accordance with an indicated dose or penetration depth.

Furthermore, in accordance with an embodiment of the present invention, the controller is configured to control operation of the propulsion mechanism so as to control a repetition rate for generation of the pulses.

Furthermore, in accordance with an embodiment of the present invention, the reservoir includes a liquid level sensor to sense a level of the liquid in the reservoir and the controller is configured to stop operation of the propulsion mechanism when the sensed liquid level is below a threshold level.

Furthermore, in accordance with an embodiment of the present invention, the reservoir and the conduit are enclosed within the handheld unit.

Furthermore, in accordance with an embodiment of the present invention, the reservoir occupies a space between the plunger and a wall of the handheld unit.

Furthermore, in accordance with an embodiment of the present invention, the cell occupies a constricted neck at a distal end of the handheld unit.

Furthermore, in accordance with an embodiment of the present invention, the conduit is interior to the plunger.

There is further provided, in accordance with a embodiment of the present invention, a method for repetitive needleless injection of a liquid into a surface, the method including: placing a nozzle of a handheld unit of a needleless injection device at the surface, the device including a cell that is filled with the liquid; and operating a controller of the device to repeatedly cause a propulsion mechanism of the device to apply a sequence of pressure pulses to the liquid, each pulse of the sequence of pressure pulses to eject a micro-jet of the liquid from the cell via an orifice in the nozzle with sufficient velocity to enable the micro-jet to penetrate into the surface, the liquid that is ejected from cell in the micro-jet the being replaced via a conduit from a reservoir.

BRIEF DESCRIPTION OF THE DRAWINGS

In order for the present invention, to be better understood and for its practical applications to be appreciated, the following Figures are provided and referenced hereafter. It should be noted that the Figures are given as examples only and in no way limit the scope of the invention. Like components are denoted by like reference numerals.

DETAILED DESCRIPTION OF THE INVENTION

Figure 1:
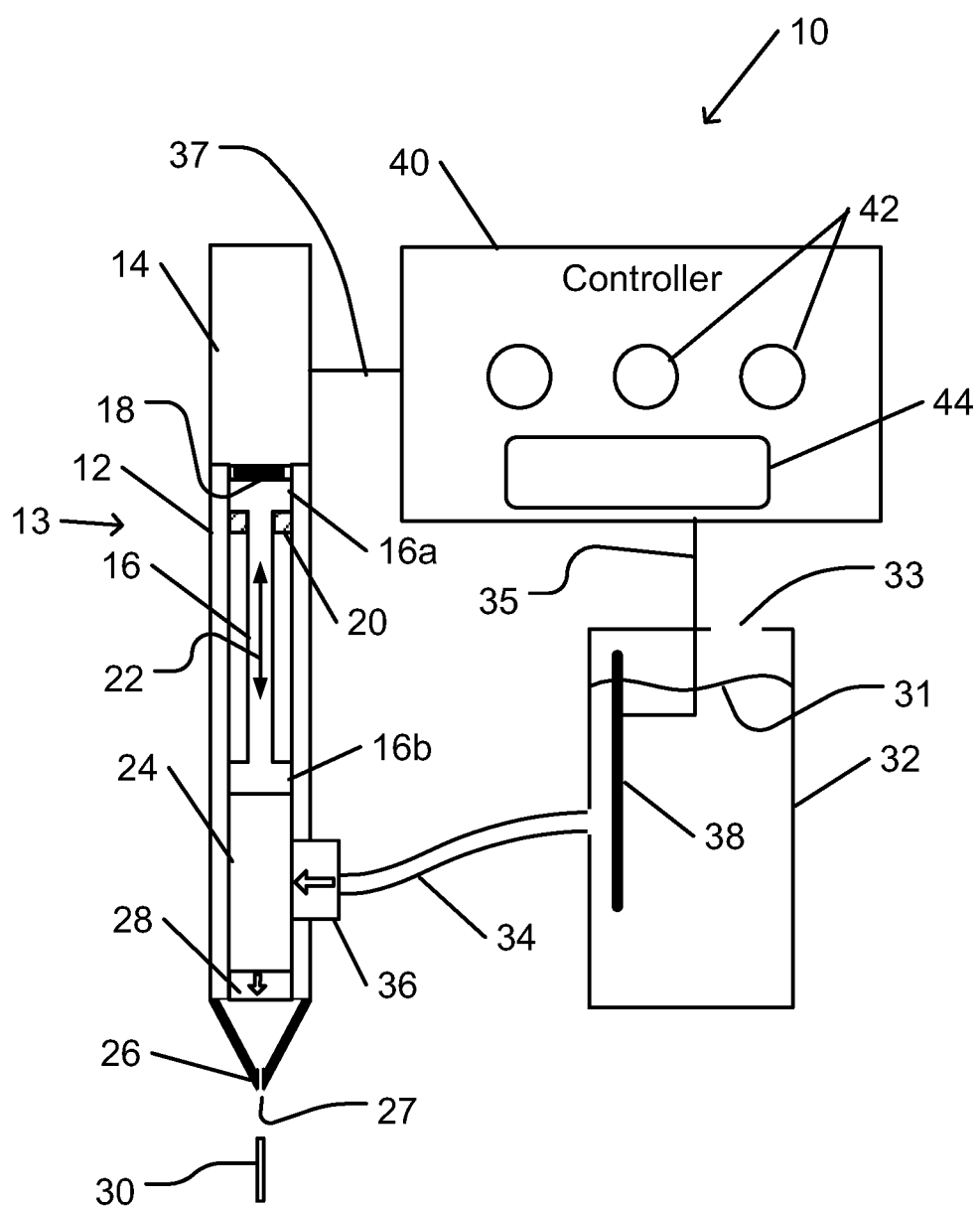
FIG. 1 schematically illustrates a repetitive needleless injection device, in accordance with an embodiment of the present invention.

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium (e.g., a memory) that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, the conjunction "or" as used herein is to be understood as inclusive (any or all of the stated options).

In accordance with an embodiment of the present invention, a repetitive needleless injection device is configured to repeatedly expel a sequence of micro-jets of a liquid. The liquid may contain (e.g., as a solution or suspension) a material that is to be introduced into the skin. The micro-jets are expelled from a nozzle with sufficient force or velocity such that the expelled liquid may penetrate into skin to a required depth. The material, such as a pigment, dye, or medication, may thus be delivered to a sufficient depth beneath the skin surface so as to function in an intended manner. For example, a dye may be injected to a sufficient depth so as to permanently color the skin to form permanent makeup or a tattoo. A medication may be injected to sufficient depth so as to be absorbed into the blood stream or otherwise effect an intended treatment.

A device that injects fluids into the skin without the use of needle that penetrates the skin surface may be advantageous. A needleless device may reduce or eliminate physical or psychological trauma, such as bleeding, that is sometimes associated with the use of hypodermic needles. Needleless delivery may reduce or eliminate the risk of infection or injury that may sometimes accompany use of needles. In some applications, use of a needleless device may enable safe reuse of the equipment, at least reducing some of the expense or complications (e.g., ensuring timely delivery to remote locations, eliminating the expense of needle replacement and of special disposal of sharp objects, reduction of maintenance costs) that may be associated with the use of disposable needles. Needleless delivery may enable achieving a desired result using less liquid and in less time than would be required using a needle. For example, in cosmetic applications, such as application of permanent makeup, the quantity of pigment may be less than with the use of needles.

Typically, a device that utilizes a needle cannot be safely moved at times when the needle is inserted into the skin. As a result, a person who manipulates a needle device may have to reposition the needle device manually for each application. For example, dots of pigment may be applied to a bald area of a scalp to simulate hair. With a needle, the applier would have to manually move the needle to each location where a dot is to be applied. As a result, the dots may not be evenly distributed over the scalp. On the other hand, a needless delivery device in accordance with an embodiment of the present invention may be moved continuously during application of the dots. For example, a skilled operator may be able to move the device at a constant speed during application. As a result, the dots may be evenly distributed over the scalp. Similar considerations may be relevant to other applications of delivery of a liquid substance to a skin surface.

A repetitive needleless injection device in accordance with an embodiment of the present invention includes a pressure cell. A propulsion mechanism is configured to apply pulses of pressure to a liquid that fills the pressure cell. The pressure pulses may expel micro-jets of the liquid via a dispenser nozzle of the cell. When the dispenser nozzle is placed against a skin surface, the expelled micro-jet may penetrate into the skin. Thus, the liquid may be introduced into the skin without the use of a needle.

For example, a propulsion mechanism may include an impulse generator and a plunger. The impulse generator is configured to generate the impulses. The plunger is configured to move linearly to transmit the impulses to the cell to produce pressure pulses in the liquid in the cell. A distal end of the plunger may form a proximal wall of the pressure cell. (As used with respect to the structure of the repetitive needleless injection device, the distal direction is the direction toward the dispenser nozzle. When the repetitive needleless injection device is in use, the distal direction equivalently refers to a direction toward the skin surface into which the liquid is to be introduced. The proximal direction refers to the direction toward the propulsion mechanism or, equivalently, toward a hand or holder that is holding or manipulating the repetitive needleless injection device when in use.)

When applying a pulse, the impulse generator may rapidly push the plunger in the distal direction. For example, an active surface of the impulse generator may be displaced distally to push the plunger in the distal direction. The plunger may thus rapidly increase the pressure of the liquid in the pressure cell sufficiently above atmospheric pressure so as to forcefully expel a micro-jet of the liquid out of the dispenser nozzle.

After expulsion of the micro-jet, the active surface of the impulse generator may retract in the proximal direction. For example, the coupling of the active surface with the plunger may be such that the retraction of the active surface retracts the plunger in the proximal direction. As another example, a separate retraction or retention mechanism may proximally retract the plunger when not forced to move distally by action of the impulse generator. The retraction of the plunger may create suction within the pressure cell. As a result, liquid may be drawn into the pressure cell from a reservoir of the liquid in order to replace the volume of liquid that was expelled in the micro-jet.

The dispenser nozzle may be provided with a unidirectional valve that enables expulsion of the micro-jet while preventing entry of gasses or other fluids from the ambient atmosphere. Thus when the plunger is retracted, the suction may draw liquid from the reservoir, rather than drawing gasses from the ambient atmosphere inward via the nozzle. Alternatively or in addition, adhesive forces and surface tension at the nozzle may be sufficient to block entry of gasses via the nozzle during retraction of the plunger.

For example, a unidirectional valve may include an aperture and a stopper (e.g., in the form of a ball or having another form) on the downstream side of the aperture. Downstream is used herein in relation to flow in a forward, allowed direction. When a forward flow of fluid flows through the aperture in the forward direction, the stopper may be pushed away from the aperture, enabling forward flow through the aperture. When a backward flow fluid flows in the opposite, backward direction, the stopper is pushed against the aperture, impeding or blocking flow through the aperture. A mechanism may be provided to return the stopper to the aperture after cessation of the forward flow or to prevent excessive separation between the aperture and the stopper. For example, a spring or other elastic element may be configured to push or pull the stopper to the aperture. The stopper and aperture may include a ferromagnetic material, with at least one of the stopper and aperture being magnetized.

The impulse generator may include a piezoelectric actuator, a magnetostrictive actuator, or similar actuator with a cycle time that is short enough to enable a suitable repetition rate. As used herein, a cycle time refers to the period of time from application of a pressure pulse until the repetitive needleless injection device and the impulse generator are ready to apply another pulse. Thus, the repetition rate is equal to the inverse of the cycle time. For example, if the cycle time is about 1 millisecond, as is typical for a piezoelectric actuator, then the repetition rate may be up to about 1000 Hz.

A piezoelectric actuator may include a piezoelectric crystal that is coupled to a mechanical amplifier. For example, a mechanical amplifier may include an elliptical cell or a lever arrangement, as is known in the art. The mechanical amplifier may be configured to convert a small displacement of a surface of the piezoelectric crystal that is applied to one part of the mechanical amplifier into a larger displacement that is applied to the plunger. Similarly another type of actuator (e.g., a ferromagnetic mass of a magnetostrictive actuator) may include a mechanical amplifier. Another type of actuator may be used.

Components of a repetitive needleless injection device in accordance with an embodiment of the present invention may be enclosed in a handheld and manipulable casing. For example, the casing may be in the form of a pen or pistol with the dispenser nozzle at the distal end. Or example, the handheld casing may enclose at least the dispenser nozzle, the pressure cell, the plunger, and the impulse generator.

The outer surface of the handheld casing may include one or more controls for user control of operation of the repetitive needleless injection device. Alternatively or in addition, some or all controls may be mounted on a separate unit, such as a controller of the repetitive needleless injection device.

For example, the controls may include an activate control that may be operated to start or stop operation of the impulse generator to repetitively expel micro-jets of liquid (e.g., a pushbutton or lever that may be depressed to activate the impulse generator, and which may be released to stop operation of the impulse generator). Operation of a power (e.g., on/off or off/standby) control may connect or disconnect an electrical power supply (e.g., battery or connection to power mains, driver, or to other external power supply) to or from the repetitive needleless injection device (e.g., disconnecting the power supply in an off state and connecting in an on or standby state). Other controls may be operated to control operation of the repetitive needleless injection device. For example, controls may be operated to control one or more of a repetition rate of the impulse generator, a penetration depth (e.g., determined at least in part by a speed of expulsion of the micro-jet, or by another property of the micro-jet or characteristic of operation of the impulse generator), a dose (e.g., determined at least in part by one or more of the repetition rate, a micro-jet volume, or by other parameters), or other characteristics of the injection of the liquid into the skin.

In some cases, the handheld casing may enclose at least some components of a controller for controlling operation of the repetitive needleless injection device. Where components of the controller are external to the handheld casing, the external controller components may be connected to one or more components within the handheld casing via a wired or wireless communications channel. Some components of a power supply for operation of electrically powered components of the repetitive needleless injection device (e.g., the impulse generator) may be enclosed within the handheld casing, or may be external to the handheld casing.

A reservoir of liquid for replenishing the pressure cell after expulsion of a micro-jet may be external to the handheld casing. In this case the reservoir may be connected to the pressure cell via a flexible conduit. For example, the conduit may include flexible plastic tubing or other flexible material, or include rigid tubes connected at flexible joints. One or more of a connection of the reservoir to the conduit, a connection of the conduit to the pressure cell, or a point within the conduit may include a unidirectional valve. The unidirectional valve may prevent liquid flow from the pressure cell to the conduit when the impulse generator applies a pressure pulse to the pressure cell. Thus, the pressurized liquid may exit from the pressure cell only via the dispenser nozzle. On the other hand, the unidirectional valve may enable unimpeded flow of liquid from the reservoir and conduit and into the pressure cell when suction is applied to the pressure cell. Thus, the liquid in the pressure cell may be replenished from the reservoir after expulsion of a micro-jet.

Alternatively or in addition, the reservoir may be internal to the handheld casing. For example, the reservoir may occupy a space between the plunger and the outer walls of the handheld casing. In this case, the reservoir is located within the handheld casing proximal relative to the pressure cell. The pressure cell may occupy a distal end of the handheld casing (e.g., a constricted neck of the casing at a distal end of the handheld casing). A conduit may be incorporated within the plunger. At least An opening of the conduit may be open to the reservoir. Thus, liquid may flow from the reservoir via the conduit into the pressure cell. On the other hand, when the plunger is pushed in the distal direction to expel a micro-jet, a unidirectional valve at the distal end of the conduit may prevent backflow of liquid from the pressure cell into the conduit.

Figure 2:
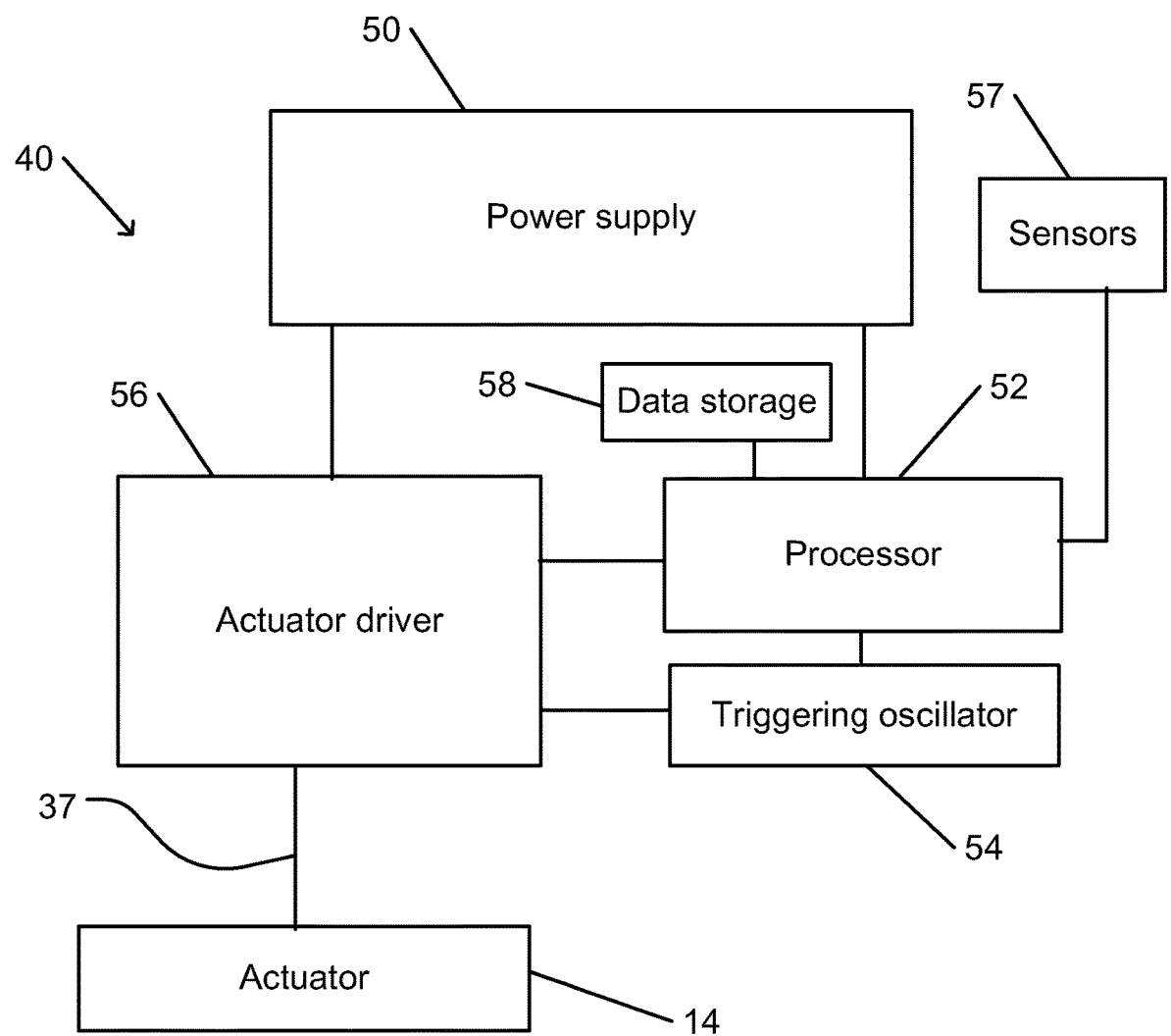
FIG. 2 schematically illustrates a controller of the repetitive needleless injection device shown in FIG. 1.

FIG. 1 schematically illustrates a repetitive needleless injection device, in accordance with an embodiment of the present invention. FIG. 2 schematically illustrates a controller of the repetitive needleless injection device shown in FIG. 1.

Repetitive needleless injection device 10 includes handheld unit 12. Although components of repetitive needleless injection device 10 are shown in the schematic drawing as outside of handheld unit 12, at least in some cases, those components may be enclosed within handheld unit 12.

Handheld unit 12 includes a casing that encloses components of repetitive needleless injection device 10 that are operable to repetitively eject a series of liquid micro-jets 30. Handheld unit 12 may have the general form of an elongated cylinder. For example, the shape of handheld unit 12 may be similar to that of a pen, syringe, pistol barrel, or similar handheld or manipulable object. When components of repetitive needleless injection device 10 are not enclosed within handheld unit 12, handheld unit 12 may be connected to those external components via a suitable flexible connection. The flexible connection may be configured to enable sufficiently free manipulation of handheld unit 12 so as not to impede injection of material contained in liquid micro-jets 30 into the skin in a predetermined set of applications.

Handheld unit 12 encloses propulsion mechanism 13 and pressure cell 24. Propulsion mechanism 13 is configured to apply a series of pressure pulses to a liquid that fills pressure cell 24. As a result of application of each pressure pulse, a liquid micro-jet 30 may be ejected from pressure cell 24 via dispenser nozzle 26.

Propulsion mechanism 13 includes impulse generator 14 and plunger 16. Impulse generator 14 includes an actuator that is operable to produce an impulse (e.g., move a surface such as actuation surface 18 in a linearly outward direction). Plunger 16 is configured to be displaced linearly so as to transmit the impulse to pressure cell 24.

Plunger 16 is configured to move linearly back and forth within a longitudinal dimension of handheld unit 12, as indicated by piston motion arrow 22. Plunger 16 is configured to move in a distal direction (toward nozzle 26) in response to a displacement of actuation surface 18 of impulse generator 14. Impulse generator 14 is configured to displace actuation surface 18 in response to a driver signal that is generated by actuator driver 56 of controller 40 of repetitive needleless injection device 10. Actuator driver 56 may generate driver signals with a repetition rate that is determined by operation of triggering oscillator 54 of controller 40.

Actuator driver 56 may control operation of impulse generator 14 via actuator connection 37. For example, actuator connection 37 may include an electric cable, e.g., a lightweight electric cable. In some cases, e.g., where handheld unit 12 includes a self-contained power supply, actuator connection 37 may include a wireless connection.

For example, impulse generator 14 may include a piezoelectric actuator, a magnetostrictive actuator, pulsed laser and a material that is configured to expand upon absorption of a laser pulse, an actuated high-pressure vessel, a linear electromagnetic motor, a compressed mechanical spring, or another type of actuator that may be driven at a suitable repetition rate. A preference or requirement for a particular repetition rate may be determined in accordance with an intended application of repetitive needleless injection device 10. For example, a repetition rate may be selected so as to enable delivery of a sufficient amount of a material (e.g., a dye, medication, or other material) to the skin at a desired rate (e.g., during a comfortable or natural rate of movement of handheld unit 12 over the skin surface, or an otherwise determined rate).

An impulse generator 14 in the form of a piezoelectric actuator includes a piezoelectric crystal connected to suitable electrodes. The maximum displacement of a surface of the piezoelectric crystal may not be sufficient to enable expulsion of a liquid micro-jet 30. In such a case, impulse generator 14 may include a mechanical amplifier. The mechanical amplifier is configured to produce a sufficiently large displacement of actuation surface 18 in response to a smaller displacement of a surface of the piezoelectric crystal that is applied to the mechanical amplifier. For example, actuation surface 18 may represent a surface of the mechanical amplifier with amplified displacement, or a surface that is mechanically coupled to such a surface of the mechanical amplifier. Similarly, an impulse generator 14 that includes a magnetostrictive or other type of actuator may include a mechanical amplifier.

For example, a mechanical amplifier may include an elliptical cell, an arrangement of one or more levers, or another type of mechanical amplifier. For example, the amplification factor of the mechanical amplifier may be about 10 (e.g., for a piezoelectric actuator), or another suitable amplification factor.

Actuation surface 18 is configured to apply a force to proximal end 16a to push plunger 16 in the distal direction. The force is transmitted to liquid in pressure cell 24 by distal end 16b of plunger 16. Thus, the force that is transmitted by plunger 16 may increase the pressure of the liquid in pressure cell 24 over the pressure that is applied by the ambient atmosphere.

Pressure cell 24 may be configured such that the only outlet of liquid from pressure cell 24 under application of excess pressure is orifice 27 of nozzle 26. For example, a diameter of distal end 16b of plunger 16 may be slightly less than the interior diameter of pressure cell 24. Any space between the perimeter of distal end 16b and the interior walls of pressure cell 24 may be filled with sealing structure (e.g., O-ring or other sealing structure). The sealing structure may include a low friction surface so as to prevent liquid flow between distal end 16b and walls of pressure cell 24 without unduly impeding motion of plunger 16.

Structure of pressure cell 24 or of plunger 16 may be configured to prevent backflow of liquid from pressure cell 24 to reservoir 32 during application of excess pressure to pressure cell 24. For example, an inlet conduit 34 for conducting the liquid from reservoir 32 to pressure cell 24 may include inlet unidirectional valve 36. Inlet unidirectional valve 36 may be configured to enable flow of fluid from reservoir 32 to pressure cell 24 when suction is applied to pressure cell 24, while preventing backflow of liquid from pressure cell 24 toward reservoir 32. For example, inlet unidirectional valve 36 may be located at an interface between inlet conduit 34 and pressure cell 24, as shown. Alternatively or in addition, inlet unidirectional valve 36 may be located at an interface between reservoir 32 and inlet conduit 34, or elsewhere along inlet conduit 34. Alternatively or in addition, e.g., when reservoir 32 is enclosed within handheld unit 12, one or more of reservoir 32, plunger 16, or pressure cell 24 may be configured to seal off flow between reservoir 32 and pressure cell 24 when pressure is applied to pressure cell 24.

Since the only outlet from pressure cell 24 is orifice 27 of nozzle 26, the excess pressure may force the liquid out of pressure cell 24 via orifice 27 in the form of a liquid micro-jet 30. The ejection of liquid micro-jet 30 may relieve the excess pressure in pressure cell 24, restoring an equilibrium state where the pressure of the liquid is countered by retaining forces (e.g., atmospheric pressure, adhesion, surface tension, or other forces at orifice 27).

After the distal displacement of actuation surface 18, impulse generator 14 retracts actuation surface 18 in the proximal direction (away from nozzle 26). The retraction displaces actuation surface 18 to substantially the original position of actuation surface 18 prior to the distal displacement. When actuation surface 18 is retracted, one or more restoration mechanisms similarly retract plunger 16 to its original proximal position.

For example, the restoration mechanism may include a rigid bond of plunger 16 to impulse generator 14, e.g., at actuation surface 18. The rigid bond may be formed as one piece with part of impulse generator 14 (e.g., by casting, molding, or extruding plunger 16 and a part of actuation surface 18 or of impulse generator 14 as a single piece, or by machining a single piece to form them). The rigid bond may include a bonding material (e.g., adhesive, glue, cement, epoxy, solder, or other bonding material) a mechanical fastener (e.g., screw, clamp, or other mechanical fastener), magnetic attraction, or another rigid connection. Thus, the retraction of actuation surface 18 entails retraction of the connected plunger 18. Such a rigid bond may enable precise control of the position of the plunger by controlling operation of impulse generator 14. (Such precise control may be especially advantageous in a repetitive needleless injection device 10 that does not include an outflow unidirectional valve 28.)

Alternatively or in addition, the restoration mechanism may include retraction mechanism 20. Retraction mechanism 20 may include a resilient element such as a spring or deformable gasket, a magnet, or another element, that exerts a restoring force on plunger 16 in the proximal direction. Thus, after a pushing force of actuation surface 18 on proximal end 16a of plunger 16 is released, possibly separating actuation surface 18 from plunger 16, retraction mechanism 20 may push plunger 16 in the proximal direction.

When a retraction mechanism 20 is used without a rigid connection between actuation surface 18 and plunger 16, plunger 16 may separate from actuation surface 18 after exertion of a pushing force. For example, inertial of plunger 16 may cause proximal end 16a to separate from actuation surface 18. Such separation may result in the amplitude of the motion of plunger 16 being greater than that of the motion of actuation surface 18. The increased amplitude of the displacement may further increase the amount of liquid that is forced out of nozzle 26 by application of the pressure. Furthermore, the separation may increase the rate of application of the excess pressure to pressure cell 24. The increase in rate of application of excess pressure may enable ejection of liquid micro-jet 30 with increased velocity. The increased velocity of liquid micro-jet 30 may increase the depth of penetration of liquid micro-jet 30 into the skin. The increased volume of liquid micro-jet 30 may increase the resultant dose to the skin of a material that is delivered by liquid micro-jet 30.

Retraction of plunger 16 by the restoration mechanism after expulsion of liquid micro-jet 30 may create suction in pressure cell 24. The suction may draw liquid from reservoir 32 into pressure cell 24 via inlet conduit 34 and inlet unidirectional valve 36. Alternatively or in addition, when plunger 16 is retracted, liquid may flow from reservoir 32 into pressure cell 24 via one or more openings that are opened by retraction of plunger 16.

Inflow of air via orifice 27 of nozzle 26 during application of suction to pressure cell 24 may be prevented by outlet unidirectional valve 28 that is configured to control flow through nozzle 26. Outlet unidirectional valve 28 is configured to enable expulsion of a liquid micro-jet 30 from pressure cell 24 through orifice 27 when excess pressure is applied to pressure cell 24. Outlet unidirectional valve 28 is also configured to prevent inflow, e.g., of atmospheric air, through orifice 27 of nozzle 26 into pressure cell 24 when suction is applied to pressure cell 24. Thus, when suction is applied to pressure cell 24, inflow is enabled only from reservoir 32.

Alternatively or in addition to action of outlet unidirectional valve 28, inflow of air through orifice 27 of nozzle 26 and into pressure cell 24 during application of suction to pressure cell 24 may be prevented by adhesive forces and surface tension (or, collectively, capillary forces) that act on liquid in orifice 27. If the force of the applied suction on liquid in orifice 27 is less than the capillary forces, inflow of air through orifice 27 may be prevented. In this case, outlet unidirectional valve 28 may not be needed. For example, the capillary force may be expressed as $H\gamma \cos\theta$, where H is the circumference of the inner surface of orifice 27, $\gamma$ is the surface tension of the liquid in orifice 27 (e.g., in units of force per length), and $\theta$ is the fluid contact angle of the liquid in orifice 27 with the interior walls of orifice 27 (dependent on adhesive forces between the liquid and the material of the interior wall of orifice 27).

The flow of liquid from reservoir 32 into pressure cell 24 may replace the volume of liquid that was ejected from pressure cell 24 in liquid micro-jet 30. Replenishing the liquid in pressure cell 24 may restore pressure cell 24 to an equilibrium state.

A cycle of operation of repetitive needleless injection device 10 includes operation of pushing plunger 16 to apply a pulse of excess pressure to pressure cell 24 to expel a liquid micro-jet 30, and retraction of plunger 16 to create a suction to replenish the supply of liquid in pressure cell 24. The time required to complete this cycle is the cycle time of repetitive needleless injection device 10. For example, the cycle time may be about 1 millisecond. In this case, the maximum repetition rate for a series of cycles is about 1000 hertz. A repetition rate of about 1000 Hz may be sufficient to apply a dye at a rate that is suitable for such applications as application of permanent makeup or tattooing. Other repetition rates may be suitable for other applications (e.g., delivery or a drug or other therapeutic substance).

Reservoir 32 may include a liquid container vessel that is open to atmospheric pressure at opening 33. In this case, reservoir 32 may include a stationary container that is connected to pressure cell 24 by a flexible inlet conduit 34. For example, a flexible inlet conduit 34 may include a tube that is made of a flexible plastic or similar material. Alternatively or in addition, inlet conduit 34 may be constructed of a plurality of rigid tubes that are connected by flexible joints. The flexibility of inlet conduit 34 may enable free manipulation of handheld unit 12 while maintaining the fluid connection of pressure cell 24 to reservoir 32.

When reservoir 32 is open to atmospheric pressure and enclosed within handheld unit 12, opening 33 may be located on a side of handheld unit 12 that is designated to face upward. For example, handheld unit 12 may include a grip or other structure to facilitate maintaining an orientation of handheld unit 12 where opening 33 faces upward. Alternatively or in addition, opening 33 may be provided with baffles, unidirectional valves, or other structure to inhibit or prevent outward spillage of liquid from reservoir 32 via opening 33. In some cases, opening 33 may be covered by a flexible membrane that transmits pressure while preventing spillage.

In some cases, reservoir 32 may be provided with a liquid level sensor 38 to measure liquid level 31 of liquid in reservoir 32. For example, liquid level sensor 38 may be configured to generate a signal that is indicative of a sensed position (e.g., indicated by a sensed height, volume, pressure, electrical resistance, dielectric constant, radiation attenuation, refraction, heat conduction, or other quantity that may be indicative of liquid level 31) of liquid level 31. The generated signal may be transmitted via sensor connection 35 to controller 40. Sensor connection 35 may include an electric cable (e.g., a lightweight cable for transmitting a low voltage signal) or a wireless connection. Alternatively or in addition, a counter or counting mechanism or function may be provided to count the number of pulses that were applied by operation of impulse generator 14. If at least an approximate volume of each ejected micro-jet 30 is known, a volume of the liquid that remains in reservoir 32 may be estimated.

Controller 40 (e.g., circuitry of controller 40 or a processor 52 of controller 40 operating in accordance with programmed instructions that are stored on data storage device 58) may be configured to stop operation of impulse generator 14 (e.g., by controlling operation of triggering oscillator 54 or of actuator driver 56) when liquid level 31 falls below a predetermined value. For example, the predetermined value may be a level that is sufficient to prevent air bubbles from forming in inlet conduit 34 or in pressure cell 24.

Alternatively or in addition, controller 40 may be configured to generate an alert when liquid level 31 falls below a predetermined threshold level. For example, the generated alert may be output (e.g., by producing a visible or audible indication using output device 44) to inform a user of repetitive needleless injection device 10 that liquid level 31 is low. The user may stop operation of impulse generator 14 (e.g., by operating one or more user controls 42), may replenish the supply of the liquid in reservoir 32, may replace reservoir 32, or may perform another action in response to the generated alert.

Components of controller 40 may be external to handheld unit 12. For example, controller 40 may be connected to handheld unit 12 by a flexible wire or cable, or via a wireless connection. Alternatively or in addition, components of controller 40 may be enclosed within or mounted to handheld unit 12.

Controller 40 includes power supply 50. For example, power supply 50 may include one or more batteries, photovoltaic cells, or another self-contained power source. Power supply 50 may include one or more transformers or power converters to convert an electrical power signal from an external power source, e.g., from an electrical mains, generator, photovoltaic array, or another external power source to a power signal that is suitable for operation of one or more components of repetitive needleless injection device 10. In the case that components of controller 40 communicate wirelessly with components of handheld unit 12, handheld unit 12 may be directly provided with a separate supply of electric power (or a component of power supply 50).

Controller 40 may include a processor 52. For example, processor 52 may include one or more processing units, e.g. of one or more computers, that are configured to operate in accordance with programmed instructions. Alternatively or in addition, processor 52 may include analog or digital circuitry that is configured to perform one or more operations, e.g., in a fixed manner in accordance with one or more input parameter values that are selected by operation of user controls 42.

In some cases, a processor 52 in the form of a processing unit may communicate with data storage device 58. Data storage device 58 may include one or more fixed or removable, volatile or nonvolatile memory or data storage units. Data storage device 58 may include a computer readable media. Data storage device 58 may be utilized to store programmed instructions for operation of processor 52, data or parameters for use by processor 52 during operation, or results of operation of processor 52.

Processor 52 may be configured to receive signals from one or more sensors 57. For example, sensors 57 may include liquid level sensor 38. Sensors 57 may include one or more sensors that measure one or more conditions that could affect operation of repetitive needleless injection device 10. For example, sensors 57 may be configured to measure one or more of a temperature (e.g., of the ambient atmosphere, of liquid in pressure cell 24, of the skin, or other temperature), a barometric pressure, relative humidity, a light or color sensor (e.g., to monitor delivery of a dye to the skin), a flowmeter (e.g., in inlet conduit 3 or elsewhere), a sensor to measure a property of a liquid in pressure cell 24 or in reservoir 32 (e.g., electrical or thermal conductivity, density, viscosity, pressure, color, or another property), or other relevant properties. Processor 52 may be configured to control operation of repetitive needleless injection device 10 in accordance with the sensed values. A processor 52 in the form of a processing unit may be configured to interpret signals that are received from sensors 57 to obtain a measured value, to store signals or measured values on data storage device 58, or to utilize the measured values in controlling operation of one or more components of repetitive needleless injection device 10.

Processor 52 may be configured to operate triggering oscillator 54. Triggering oscillator 54 may include one or more clock circuits or oscillator devices. A frequency of operation of triggering oscillator 54 may be adjustable, e.g., by operation of one or more user controls 42. Adjustment of an oscillation rate of triggering oscillator 54 may determine a repetition rate for operation of impulse generator 14 of repetitive needleless injection device 10.

User controls 42 may include one or more dials, pushbuttons, switches, levers, sliders, knobs, keys, touch screens, pointing devices, keyboards, keypads, microphones, or other devices that are operable by a user to control operation of controller 40 and of repetitive needleless injection device 10. For example, user controls 42 may be operated to adjust one or more parameters that determine a state of repetitive needleless injection device 10 (e.g., operate, standby, off, or another state), delivered dose, a penetration depth of a delivered substance into the skin, a repetition rate, a threshold liquid level, or another parameter of operation of repetitive needleless injection device 10.

A current setting may be displayed or otherwise output, e.g., via output device 44. Output device 44 may include one or more display screens, display panels, indicator lamps, speakers, printers, bells, buzzers, vibrators, or another device capable of producing visible, audible, or tactile output.

Processor 52 may be configured to operate actuator driver 56. Operation of actuator drive 56 may cause propulsion system 13 to generate a series of impulses that are applied to pressure cell 24. An impulse may be characterized by a set of parameters that describe displacement of propulsion system 13 as a function of time. For example, the component may include one or more of actuation surface 18 and plunger 16 (e.g., both when rigidly connected to one another).

Figure 3:
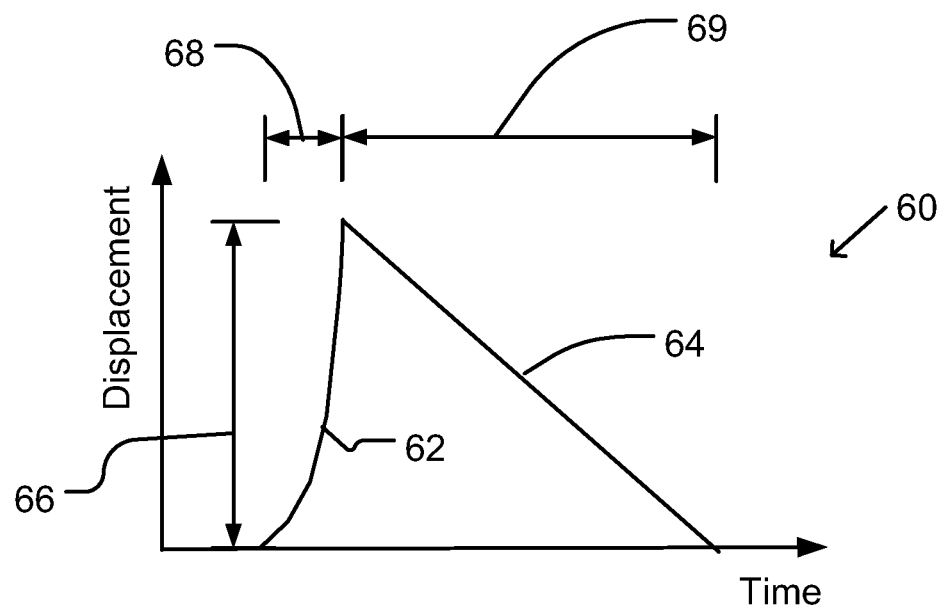
FIG. 3 is a schematic pulse profile graph showing displacement as a function of time of a component during a pulse of a propulsion system of a repetitive needleless injection device, in accordance with an embodiment of the present invention.

FIG. 3 is a schematic pulse profile graph showing displacement as a function of time of a component during a pulse of a propulsion system of a repetitive needleless injection device, in accordance with an embodiment of the present invention.

Pulse profile graph 60 shows displacement as a function of time. For example, the displacement may represent one-dimensional displacement of a part of plunger 16. Pulse profile 60 may be characterized by three parameters, rise time 68, amplitude 66, and fall time 69. A displacement in the distal direction is represented in pulse profile graph 60 as a positive displacement.

In the example shown, pulse profile 60 includes a segment that represents push phase 62. During push phase 62, a pressure pulse may be generated by displacement of plunger 16. Push phase 62 is shown as nonlinear, approximately quadratic dependence of displacement on time. For example, push phase 62 in which displacement is a quadratic function of time may represent generation of a pressure pulse by displacement of plunger 16 with an approximately constant acceleration. A constant acceleration results from application of a constant force by mechanism actuator 14 to actuation surface 18 or to plunger 16. For example, an approximately constant acceleration may be generated by applying a linearly increasing current to a piezoelectric actuator of impulse generator 14. A constant acceleration during push phase 62 may enable increased efficiency of operation of propulsion system 13 over another form (e.g., linear, representing a constant velocity generated by applying a constant current to a piezoelectric actuator of impulse generator 14) of push phase 61. Furthermore, the useful lifetime of components of propulsion system 13 may be increased when constant acceleration is applied.

Push phase 62 is characterized by a distal displacement of amplitude 66 during rise time 68. For example, rise time 68 may be approximately 10 microseconds, or another value.

The size of amplitude 66 may determine a volume of liquid micro-jet 30. For a constant cross sectional area of pressure cell 24, a volume of liquid that is ejected in liquid micro-jet 30 during push phase 62 is proportional to amplitude 66. The volume of liquid in liquid micro-jet 30 is thus controllable by controlling amplitude 66.

The rate at which liquid micro-jet 30 is ejected is proportional to rise time 68. The rate of ejection may determine a velocity of an ejected liquid micro-jet 30. The velocity of liquid micro-jet 30 may, in turn, determine of depth of penetration into the skin of a substance that is delivered by liquid micro-jet 30.

Pulse profile 60 includes a segment that represents retraction phase 64 after ejection of liquid micro-jet 30. During retraction phase 64, plunger 16 is retracted to its start position (prior to commencement of push phase 62) during fall time 69. Fall time 69 may be determined by properties of a restoration mechanism (e.g., of retraction mechanism 20) of propulsion system 13. During fall time 69, suction may be applied to pressure cell 24. During fall time 64, the applied suction may cause pressure cell 24 to replace the volume of liquid that was expelled in liquid micro-jet 30 with liquid from reservoir 32. Fall time 69 may be sufficiently long so to avoid formation of bubbles (e.g., by cavitation or leakage) in pressure cell 24 or in inlet conduit 34. On the other hand, fall time 69 may be sufficiently short so as to avoid excessive elongation of the cycle time of propulsion system 13. For example, the length fall time 69 may be about one millisecond, or another value.

User controls 42 may be operated to set one or more parameters of operation of repetitive needleless injection device 10. Typical operational parameters may include dose, penetration depth, repetition rate, and liquid level. Additional parameters may be input by a user operating user controls 42, may be stored on data storage device 58, may be obtained from one or more sensors 57, or may be otherwise obtained. Such additional parameters may define a type of substance (or properties of the substance), a concentration of the substance in liquid contents of pressure cell 24 and reservoir 32, characteristics of repetitive needleless injection device 10 or of handheld unit 12 (e.g., cross sectional area of pressure cell 24), or other parameters or characteristics of the substance, a liquid carrier of the substance, an ambient environment, or of structure or operation of repetitive needleless injection device 10. Processor 52 may interpret the operation of user controls 42 to obtain the set parameters. Processor 52 may apply the parameters in operation of one or more components of repetitive needleless injection device 10.

For example, in order to deliver a specified dose of a substance at a particular depth within the skin, processor 52 may control operation of one or more of actuator driver 56 and triggering oscillator 54. For example, operating actuator driver 56 to control amplitude 66 of a pulse may determine the volume of the liquid, or of a substance that is carried by the liquid, that is ejected in each liquid micro-jet 30. Operating actuator driver 56 to control rise time 68 of a pulse may determine a velocity of expulsion of liquid micro-jet 30. The velocity of expulsion of liquid micro-jet 30 may affect the penetration depth into the skin. Controlling a frequency of triggering oscillator 54 may control a repetition rate of expulsion of liquid micro-jets 30. The repetition rate may affect the total dose that is applied to an area of skin when nozzle 26 is held at a single position on the skin or is moved slowly.

Parameters of design or operation of repetitive needleless injection device 10 may be selected in order to satisfy various criteria. For example, volume of each micro-jet 30 may be selected in order to deliver a substance to the skin at a particular dose rate. For example, the volume may be no larger than 10 microliters. In some cases, the volume may be less than 5 microliters. In some cases, the volume may be no larger than 1.5 microliter.

A velocity of ejection of each micro-jet 30 may be selected in order to deliver a substance to a particular depth within the skin. In some cases, penetration depth may be proportional to the square of the micro-jet velocity. For example, the ejection velocity may be at least 50 m/s. In some cases, ejection velocity may be at least 100 m/s. Different ranges of ejection velocities may be used for delivery of the substance to another type of surface other than human skin.

A set liquid level may determine or affect when processor 52 generates an alert or modifies operation of repetitive needleless injection device 10. For example, if liquid level sensor 38 senses a level that is below a threshold value determined in accordance with a liquid level parameter, an alert may be generated, actuator driver 56 or triggering oscillator 54 may be controlled to reduce a dose or repetition rate, or actuator driver 56 or triggering oscillator 54 may be controlled to stop operation of propulsion system 13.

A repetitive needleless injection device in accordance with an embodiment of the present invention may be compact. In a compact needleless injection device, reservoir 32 is enclosed within handheld unit 12. Therefore, manipulation of handheld unit 12 may not be impeded by any need to bend or avoid twisting an external inlet conduit 34. (For example, in some cases an external inlet conduit 34 may be sufficiently wide to provide an unimpeded flow of liquid from an external reservoir 32 to pressure cell 24. The walls of the external inlet conduit 34 may be sufficiently thick and stiff so as to prevent puncture and kinking)

Some or all components of controller 40 may be external to handheld unit 12. For example, a wired connection between handheld unit 12 and controller 40 may be sufficiently thin, lightweight, and flexible so as not to noticeably impede manipulation of handheld unit 12.

Figure 4A:
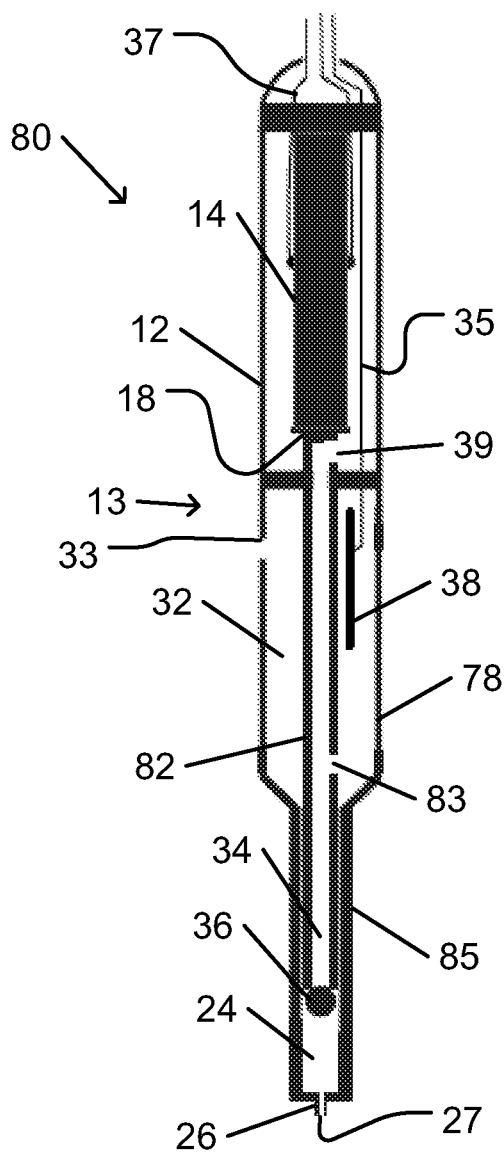
FIG. 4A schematically illustrates a compact repetitive needleless injection device, in accordance with an embodiment of the present invention.

FIG. 4A schematically illustrates a compact repetitive needleless injection device, in accordance with an embodiment of the present invention.

In compact needleless injection device 80, reservoir 32 is enclosed within handheld unit 12. For example, reservoir 32 may completely or partially fill a space between propulsion system 13 (e.g., between one or both of impulse generator 14 and plunger rod 82) and wall 78 of handheld unit 12. Opening 33 to reservoir 32 may enable refilling reservoir 32 and enables atmospheric pressure to propel liquid into pressure cell 24 when suction is applied to pressure cell 24. Opening 33 may be located on a side of handheld unit 12 that is designed to face upward. For example, handheld unit 12 may include a grip or other guiding structure to facilitate maintaining an orientation of handheld unit 12 where opening 33 faces upward. Alternatively or in addition, opening 33 may be provided with one or more of a cover, baffle, unidirectional valve, or other structure configured to impede or prevent outward spillage of liquid from reservoir 32 via opening 33.

Inlet conduit 34 for connecting reservoir 32 with pressure cell 24 is internal to plunger rod 82. The distal end of plunger rod 82 is configured to slide back and forth (distally and proximally) within distal neck 85 of handheld unit 12. The outer diameter of plunger rod 82 is sufficiently close to the inner diameter of distal neck 85 so as to prevent or impede flow of liquid between plunger rod 82 and distal neck 85. Alternatively or in addition, sealing structure may be provided to prevent flow of liquid between plunger rod 82 and distal neck 85 while enabling plunger rod 82 to slide within distal neck 85.

The distal end of distal neck 85, beyond the distal end of inlet conduit 34, forms pressure cell 24.

Inlet conduit 34 is provided with conduit opening 83. Conduit opening 83 is open to the interior of reservoir 32 to enable flow of liquid from reservoir 32 into inlet conduit 34. Air outlet opening 39 is configured to enable escape of any trapped air from inlet conduit 34 to the ambient atmosphere so as to prevent formation of bubbles in inlet conduit 34. Inlet unidirectional valve 36 the distal end of inlet conduit 34 is configured to enable outflow of liquid from inlet conduit 34 to pressure cell 24. Inlet unidirectional valve 36 is further configured to prevent liquid in pressure cell 24 from flowing into inlet conduit 34. Thus, when plunger rod 82 is pushed distally, excess pressure may be applied to liquid in pressure cell 24 so as to force a liquid micro-jet 30 to be expelled from orifice 27 of nozzle 26. When plunger rod 82 is retracted proximally, capillary forces may limit or prevent inflow of air into pressure cell 24 via orifice 27. Therefore, the retraction of plunger rod 82 may cause a suction that opens inlet unidirectional valve 36. When inlet unidirectional valve 36 is open, liquid may flow from reservoir 32 via inlet conduit 34 into pressure cell 24.

A diameter of orifice 27 may be selected in order to enable ejection of a liquid micro-jet 30 having a diameter in a predetermined range. For example, a wide diameter may enable coverage of a large area within a given period of time (e.g., when delivering a substance, such as a pigment, to a general region). On the other hand, a narrow diameter may enable drawing finer features on the skin (e.g., when delivering a substance such as a pigment to a narrow region of skin, such as the edge of an eyelid). For example, the useful diameter of orifice 27 for this application may be no wider than 300 micrometers.

For example, impulse generator 14 may include a piezoelectric actuator. The piezoelectric actuator may or may not include a mechanical amplifier. For example, in order to minimize the space occupied by impulse generator 14, a piezoelectric actuator may not include a piezoelectric crystal without a mechanical amplifier.

In compact needleless injection device 80 as shown, plunger rod 82 may be bonded to actuation surface 18 of impulse generator 14. When actuation surface 18 of impulse generator 14 is retracted in the proximal direction plunger rod 82 is also retracted.

Figure 4B:
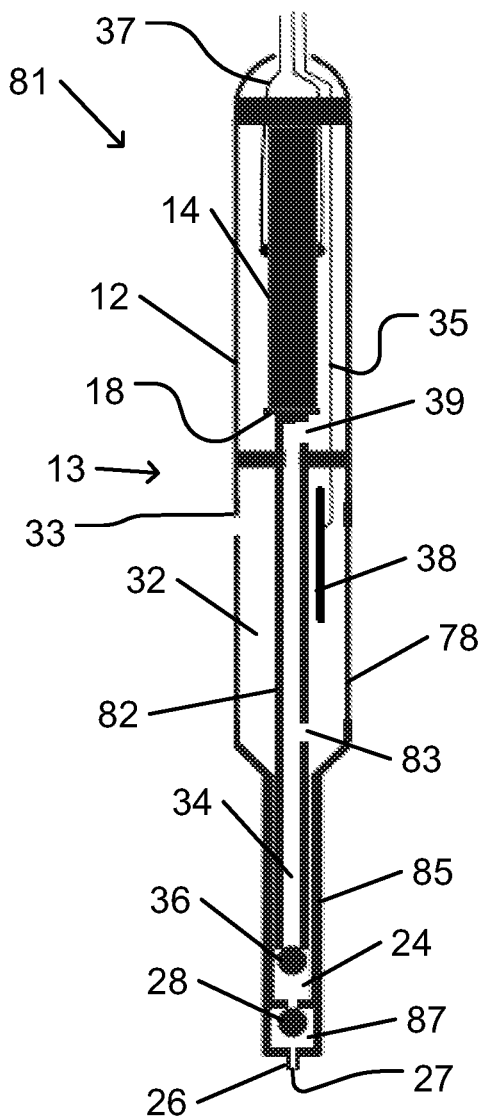
FIG. 4B schematically illustrates a compact repetitive needleless injection device as in FIG. 4A with the addition of a unidirectional valve for impeding inflow of air.

FIG. 4B schematically illustrates a compact repetitive needleless injection device as in FIG. 4A with the addition of a unidirectional valve for impeding inflow of air.

In compact needleless injection device 81, nozzle cell 87 is separated from pressure cell 24 by outflow unidirectional valve 28. Outflow unidirectional valve 28 enables liquid to flow distally outward from pressure cell 24 to nozzle cell 87 and to orifice 27 when excess pressure is applied to pressure cell 24 by plunger rod 82. On the other hand, when plunger rod 82 is retracted to apply suction to pressure cell 24, outflow unidirectional valve 28 prevents inflow of air through orifice 27 and nozzle cell 87. Thus, the suction may draw liquid from inlet conduit 34 into pressure cell 24.

Figure 5A:
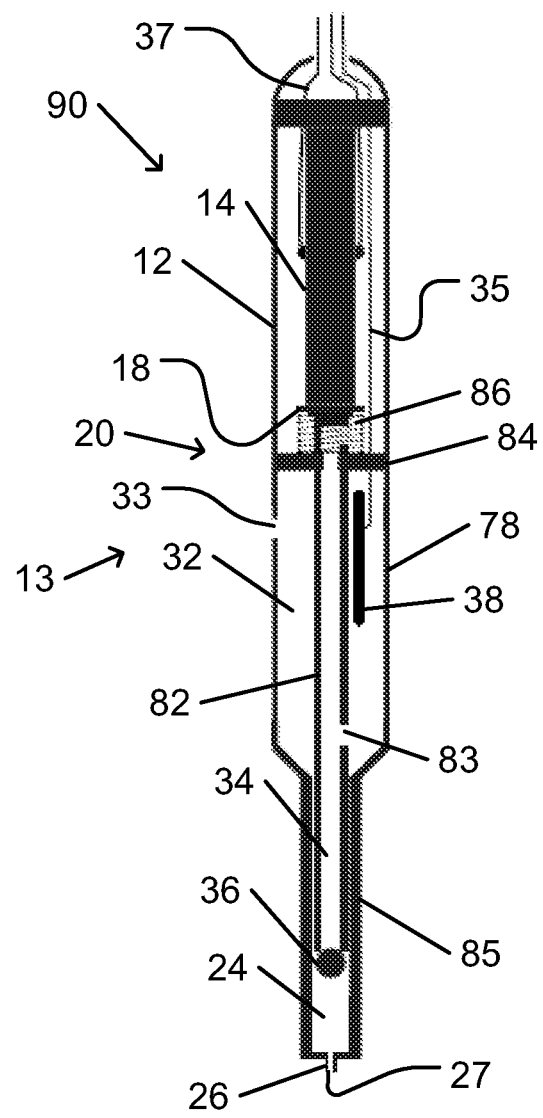
FIG. 5A schematically illustrates a compact repetitive needleless injection device as in FIG. 4A with the addition of a retaining mechanism.

FIG. 5A schematically illustrates a compact repetitive needleless injection device as in FIG. 4A with the addition of a retaining mechanism.

Compact needleless injection device 90 includes a retraction mechanism 20. Retraction mechanism 20 includes an elastic component 86 that is compressed when plunger rod 82 is pushed in the distal direction by actuation surface 18 of impulse generator 14. For example, elastic component 86 may include a spring or other resilient element that is compressible between the proximal end of plunger rod 82 and anchor 84 that is fixed to handheld unit 12. Plunger rod 82 may be retracted by re-expansion of elastic component 86 when actuation surface 18 is retracted. Thus, plunger rod 82 may be retracted without being bonded to actuation surface 18.

In some cases, whether or not the device includes a retaining mechanism, a resilient element, similar to elastic component 86, may be compressible between actuation surface 18 and anchor 84. Such a resilient element may preload a piezoelectric crystal of impulse generator 14. Such preloading may reduce mechanical shock to impulse generator 14. Reduction of shock may increase the usable lifetime of the piezoelectric crystal.

Figure 5B:
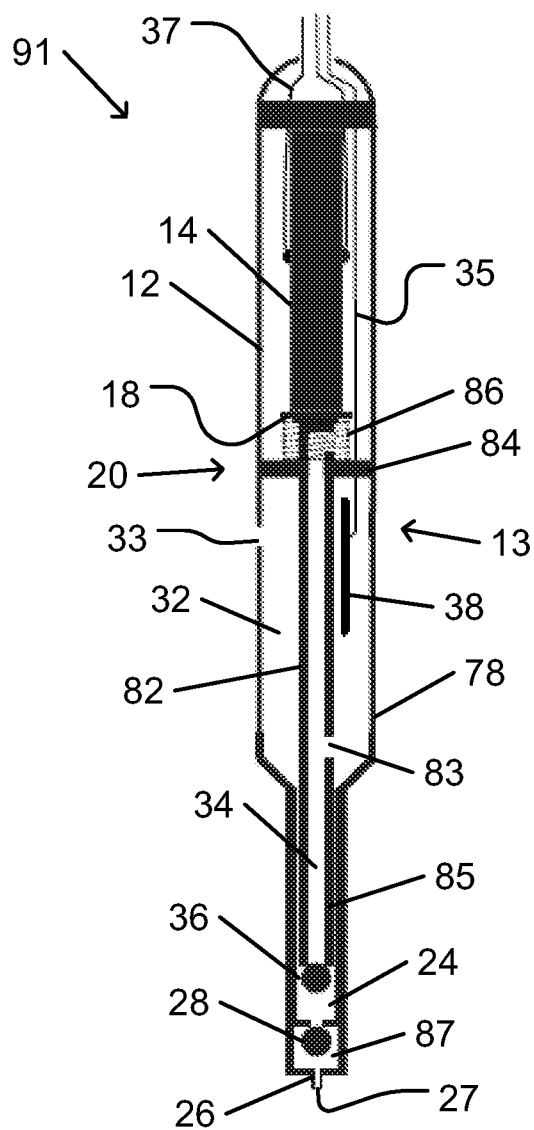
FIG. 5B schematically illustrates a compact repetitive needleless injection device as in FIG. 5A with the addition of a unidirectional valve for impeding inflow of air.

FIG. 5B schematically illustrates a compact repetitive needleless injection device as in FIG. 5A with the addition of a unidirectional valve for impeding inflow of air.

Compact needleless injection device 91 includes retraction mechanism 20 (similar to compact needleless injection device 90), together with a nozzle cell 87 and outflow unidirectional valve 28 (similar to compact needleless injection device 81).

In accordance with an embodiment of the present invention, a unidirectional valve, such as inlet unidirectional valve 36 or outflow unidirectional valve 28, may include a separable stopper on one side of an aperture. When liquid flows through the aperture toward the side with the separable stopper, the stopper separates from the aperture to enable flow through the aperture. When liquid flows toward the side of the aperture with the separable stopper, the stopper is pushed or dragged into the aperture, thus blocking flow through the aperture. For example, the separable stopper may be represented by a ball whose diameter is at least slightly larger than the diameter of the aperture.

FIGS. 6A-6E illustrate operation of unidirectional valves of a repetitive needleless injection device, in accordance with an embodiment of the present invention. For example, FIGS. 6A-6E may illustrate operation of inlet unidirectional valve 36 and outflow unidirectional valve 28 of compact needleless injection device 81 or of compact needleless injection device 91.

Figure 6A:
FIG. 6A schematically illustrates operation of a pair of unidirectional valves when no pressure is applied.

FIG. 6A schematically illustrates operation of a pair of unidirectional valves when no pressure is applied.

Inlet unidirectional valve 36 is closed, as represented by inlet valve stopper 92 in inlet valve aperture 95. Outflow unidirectional valve 28 is closed, as represented by outlet valve stopper 94 in outlet valve aperture 93. Outflow unidirectional valve 28 includes restoration element 96 for returning outlet valve stopper 94 to outlet valve aperture 93 when no forces are applied to outlet valve stopper 94. Restoration element 96 may limit opening of outflow unidirectional valve 28 to enable a rapid response to a change in applied pressure. A rapid response may limit unwanted leakage or flow through outflow unidirectional valve 28 during transition from forward to backward flow. Restoration element 96 may include, for example, a spring or a magnetic force acting between the outlet valve stopper 94 and outlet valve aperture 93. (Although a similar restoration element may be provided for inlet unidirectional valve 36, for the sake of clarity none is shown.)

Figure 6B:
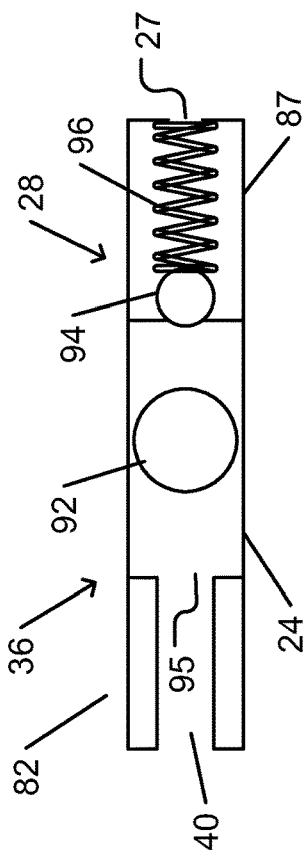
FIG. 6B schematically illustrates the unidirectional valves shown in FIG. 6A when a plunger rod is being pushed in the distal direction.

FIG. 6B schematically illustrates the unidirectional valves shown in FIG. 6A when a plunger rod is being pushed in the distal direction.

Plunger rod 82 is being pushed distally toward orifice 27. Inlet unidirectional valve 36 remains closed while outlet valve stopper 94 is pushed away from outlet valve aperture 93 by excess pressure in pressure cell 24. Thus liquid may flow from pressure cell 24 through nozzle cell 87 and out orifice 27 as a liquid micro-jet 30.

Figure 6C:
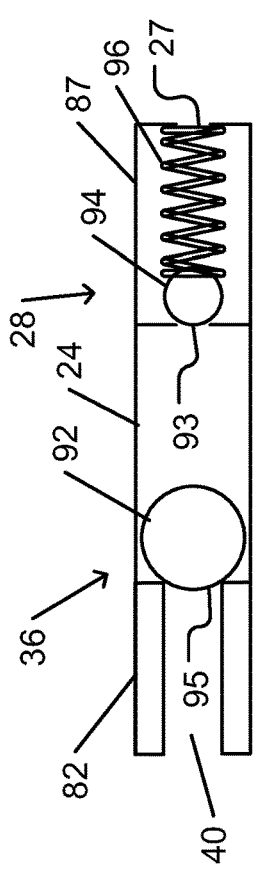
FIG. 6C schematically illustrates the unidirectional valves shown in FIG. 6B when the plunger rod has being pushed to its maximal extent.

FIG. 6C schematically illustrates the unidirectional valves shown in FIG. 6B when the plunger rod has being pushed to its maximal extent.

Inlet unidirectional valve 36 remains closed while outflow unidirectional valve 28 remains open. Liquid micro-jet 30 has been completely expelled.

Figure 6D:
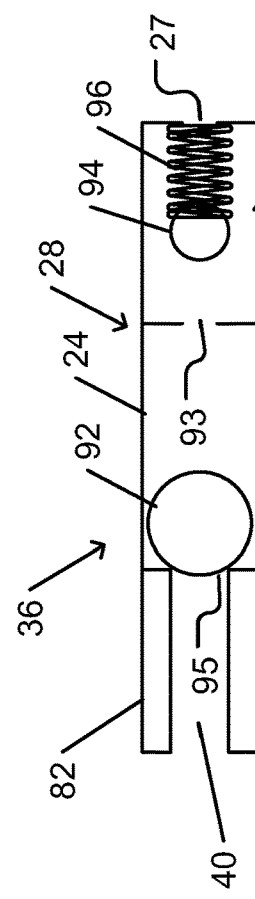
FIG. 6D schematically illustrates the unidirectional valves shown in FIG. 6C when the plunger rod is being retracted in the proximal direction.

FIG. 6D schematically illustrates the unidirectional valves shown in FIG. 6C when the plunger rod is being retracted in the proximal direction.

Outflow unidirectional valve 28 has been closed by action of restoration element 96, separating pressure cell 24 from nozzle cell 87. The retraction of inlet conduit 34 toward reservoir 32 cause liquid to flow from reservoir 32 via inlet conduit 34 into pressure cell 24. As plunger rod 82 is retracted, flow of liquid from reservoir 32 via inlet conduit 34 into pressure cell 24 may separate inlet valve stopper 92 from inlet valve aperture 95. One or more additional or alternative forces, such as suction in pressure cell 24, inertia of inlet valve stopper 92, or drag forces between pressure cell 24 and liquid in pressure cell 24, may act to separate inlet valve stopper 92 from inlet valve aperture 95.

Figure 6E:
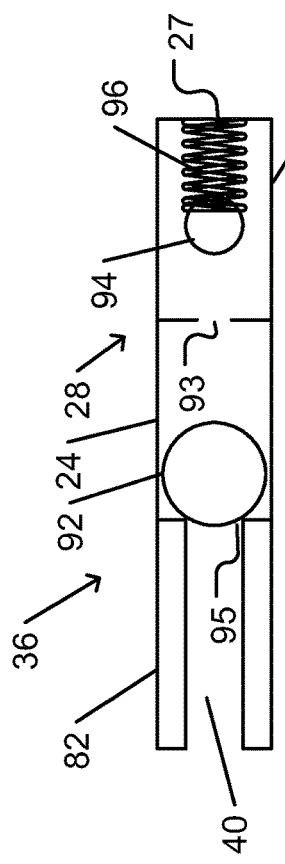
FIG. 6E schematically illustrates the unidirectional valves shown in FIG. 6D when the plunger rod has been fully retracted.

FIG. 6E schematically illustrates the unidirectional valves shown in FIG. 6D when the plunger rod has been fully retracted.

Outflow unidirectional valve 28 remains closed while inlet valve stopper 92 remains separated from inlet valve aperture 95. Liquid has ceased to flow from reservoir 32 and inlet conduit 34 into pressure cell 24.

At this point, restoration forces (e.g., a resilient element or magnetic forces) may act to return inlet valve stopper 92 to inlet valve aperture 95. When inlet valve stopper 92 has returned to inlet valve aperture 95, the state shown in FIG. 6A is restored. Thus, compact needleless injection device 81 or compact needleless injection device 91 is prepared for ejection of another liquid micro-jet 30.

A method of operation of a repetitive needleless injection device 10, in accordance with an embodiment of the present invention, may include filling reservoir 32 with a liquid that is to be injected into a surface, such as a skin surface.

Orifice 27 of nozzle 26 of the device may be placed in proximity of the surface into which the liquid is to be rejected. The distance between orifice 27 and the skin surface may be sufficiently small such that a micro-jet 30 that is ejected from orifice 27 impinges on the surface without excessive interference (e.g., slowing, distortion, spreading, or scattering) by any intervening atmosphere. On the other hand, at least a minimal gap may be maintained between orifice 27 and the surface so as to prevent contamination of the nozzle 26 by materials (e.g., bacteria or parasites) that are present on the surface. For example, the distance between orifice 27 and the surface may be no more than 5 mm. In some cases, the distance may be no greater than 3 mm.

Repetitive needleless injection device 10 may be operated to eject the micro-jets 30 liquid at a repetition rate, and each micro-jet 30 having a volume, to deliver the liquid at a particular dose rate. Repetitive needleless injection device 10 may be operated to eject each micro-jet 30 with a velocity of ejection so as to enable micro-jet 30 to penetrate the surface to a particular depth.

A piezoelectric crystal is more resistant to contraction forces than to expansion forces. Therefore, it may be advantageous to configure a needleless injection device so as to avoid internal expansion forces (e.g., following pushing of a plunger) that may disrupt the structure of the piezoelectric crystal.

Figure 7A:
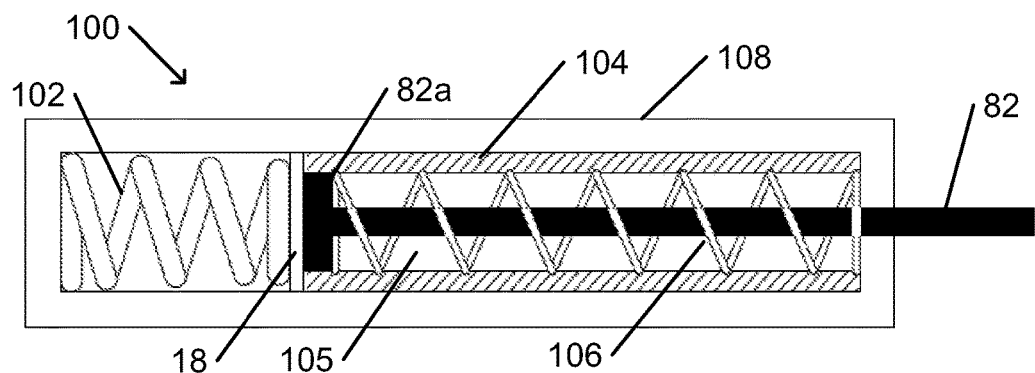
FIG. 7A schematically illustrates an alternative propulsion mechanism for the compact repetitive needleless injection device shown in FIG. 4A.

FIG. 7A schematically illustrates an alternative propulsion mechanism for the compact repetitive needleless injection device shown in FIG. 4A.

In alternative propulsion mechanism 100, hollow impulse generator 104, e.g., in the form of a hollow piezoelectric crystal, is enclosed inside mechanism housing 108. Hollow impulse generator 104 is such that plunger rod 82 may move in a longitudinal direction (distally or proximally) within longitudinal bore 105 of hollow impulse generator 104. Hollow impulse generator 104 is configured to displace activation surface 18 in the proximal direction when expanding. Propulsion spring 102 (or a similar propulsion resilient element) is confined between activation surface 18 and mechanism housing 108. Thus, proximal displacement of activation surface 18 compresses propulsion spring 102. Retaining spring 106 (or a similar resilient element) is confined between plunger head 82a and mechanism housing 108.

Figure 7B:
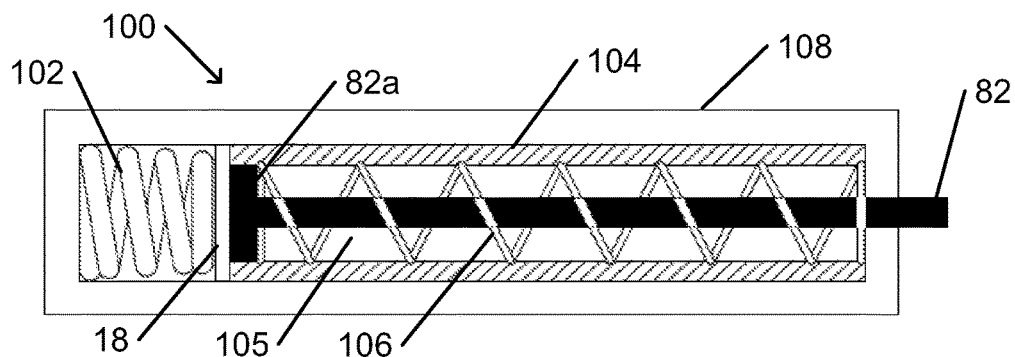
FIG. 7B schematically illustrates a plunger retraction phase of operation of the alternative propulsion mechanism shown in FIG. 7A.

FIG. 7B schematically illustrates a plunger retraction phase of operation of the alternative propulsion mechanism shown in FIG. 7A.

Hollow impulse generator 104 may be activated (e.g., by a controller) to to gradually expand to push activation surface 18 in the proximally direction, compressing propulsion spring 102. Retaining spring 106 expands to retract plunger rod 82, keeping plunger head 82a pressed against activation surface 18.

Figure 7C:
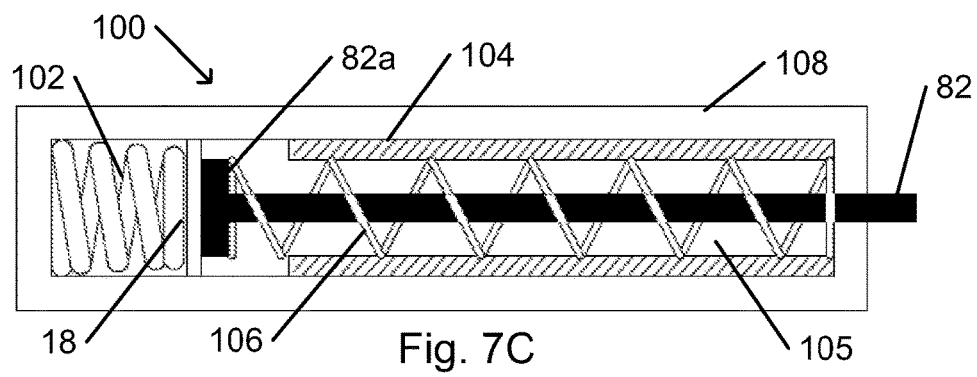
FIG. 7C schematically illustrates an impulse generator contraction phase of operation of the alternative propulsion mechanism shown in FIG. 7B.

FIG. 7C schematically illustrates an impulse generator contraction phase of operation of the alternative propulsion mechanism shown in FIG. 7B.

After plunger rod 82 has been fully retracted, hollow impulse generator 104 may be operated to rapidly contract (e.g., to its unexpanded length as indicated in FIG. 7A). The contraction of hollow impulse generator 104 is sufficiently rapid such that hollow impulse generator 104 may fully contract before re-expansion of propulsion spring 102 is able (e.g., has overcome inertia of plunger rod 82 and of propulsion spring 102) to re-extend plunger rod 82 through an appreciable displacement.

Figure 7D:
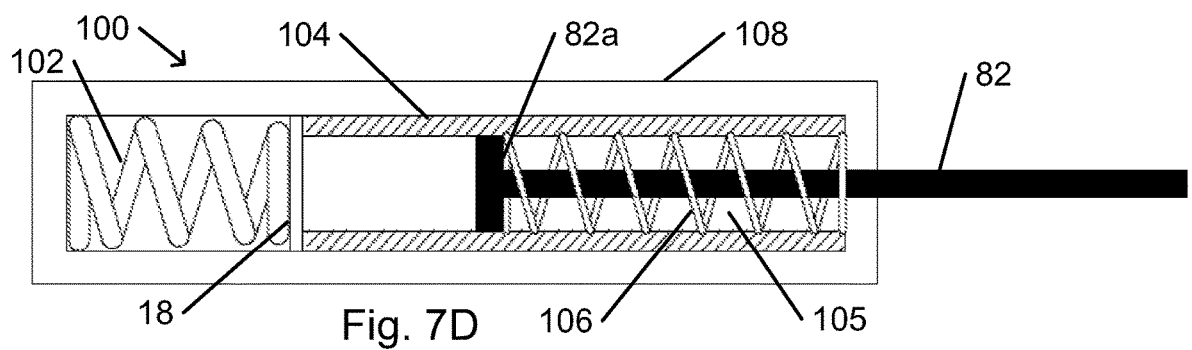
FIG. 7D schematically illustrates a plunger extension phase of operation of the alternative propulsion mechanism shown in FIG. 7C.

FIG. 7D schematically illustrates a plunger extension phase of operation of the alternative propulsion mechanism shown in FIG. 7C.

After contraction of hollow impulse generator 104, propulsion spring 102 expands to rapidly distally displace activation surface 18 to the proximal end of (contracted) hollow impulse generator 104. The rapid distal displacement of activation surface 18 distally pushes on plunger head 82a to propel plunger rod 82. The impulse that is thus applied to plunger rod 82, and the inertia of the impelled plunger rod 82, may fully extend plunger rod 82. The full extension of plunger rod 82 may compress retaining spring 106. The full extension of plunger rod 82 may cause a micro-jet of liquid to be expelled via an opening at a distal end of a compact repetitive needleless injection device that includes alternative propulsion mechanism 100.

Finally, re-expansion of retaining spring 106 may retract plunger rod 82 to its initial position (as shown in FIG. 7A)

Figure 8:
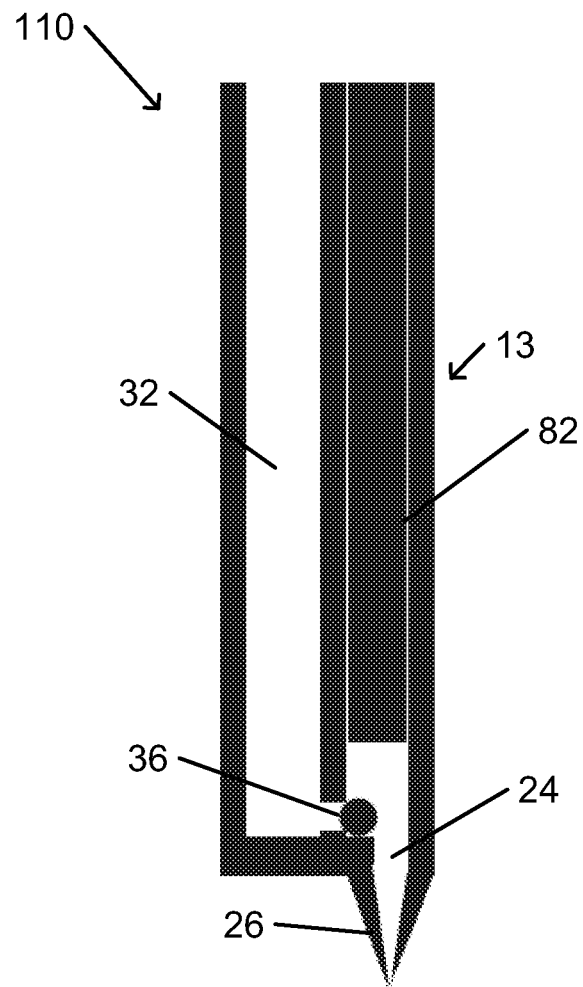
FIG. 8 schematically illustrates a compact repetitive needleless injection device with a reservoir that is not coaxial with a propulsion system.

FIG. 8 schematically illustrates a compact repetitive needleless injection device with a reservoir that is not coaxial with a propulsion system.

In non-coaxial compact needleless injection device 110, reservoir 32 is located non-collinearly with propulsion mechanism 13.

Different embodiments are disclosed herein. Features of certain embodiments may be combined with features of other embodiments; thus certain embodiments may be combinations of features of multiple embodiments. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A device for repetitive needleless injection of a liquid into a surface, the device comprising:
    a handheld unit that includes at least a cell that is fillable with the liquid, and a propulsion mechanism configured to apply a sequence of pressure pulses to the liquid, each pulse of the sequence of pressure pulses to eject a micro-jet of the liquid from the cell via an orifice between the cell and an exterior of the handheld unit with a velocity that is sufficient to enable the micro-jet to penetrate into the surface;
    a reservoir that is connected to the cell by a conduit to enable the liquid to flow from the reservoir to the cell to replace the liquid that is ejected in the micro-jet; and
    a controller that is configured to operate the propulsion mechanism repeatedly so as to eject the sequence of the micro-jets,
    wherein the propulsion mechanism comprises an impulse generator configured to displace an actuation surface to generate the pulse and a plunger configured to move linearly to transmit the pulse to the cell, and
    wherein the impulse generator is configured to expand to compress a propulsion resilient element and to contract to enable expansion of the propulsion resilient element to distally propel the plunger.

2. The device of claim 1, wherein the orifice is separated from the cell by an outlet unidirectional valve that is configured to enable flow of the liquid from the cell to the orifice and to prevent inflow from the orifice to the cell.

3. The device of claim 2, wherein the outlet unidirectional valve comprises a stopper that is separable from an aperture.

4. The device of claim 1, wherein a connection of the conduit to the cell comprises an inlet unidirectional valve to enable the liquid to flow from the conduit to the cell and to prevent backflow of the liquid from the cell to the conduit.

5. The device of claim 4, wherein the orifice is separated from the cell by an outlet unidirectional valve that is configured to enable flow of the liquid from the cell to the orifice and to prevent inflow from the orifice to the cell.

6. The device of claim 1, wherein the impulse generator comprises a piezoelectric crystal.

7. The device of claim 6, wherein the impulse generator comprises a mechanical amplifier.

8. The device of claim 1, wherein the plunger is bonded to the actuation surface.

9. The device of claim 1, wherein the plunger is provided with a retraction mechanism that is configured to retract the plunger after application of the pulse by the actuation surface.

10. The device of claim 9, wherein the retraction mechanism comprises a spring.

11. The device of claim 1, wherein the controller is configured to control operation of the propulsion mechanism so as to control one or both of an amplitude of the pulse and a rise time of the pulse.

12. The device of claim 11, wherein the controller is configured to control said one or both of an amplitude of the pulse and a rise time of the pulse in accordance with an indicated dose or a penetration depth.

13. The device of claim 1, wherein the controller is configured to control operation of the propulsion mechanism so as to control a repetition rate for generation of the pulses.

14. The device of claim 1, wherein the reservoir comprises a liquid level sensor to sense a level of the liquid in the reservoir and the controller is configured to stop operation of the propulsion mechanism when the sensed liquid level is below a threshold level.

15. The device of claim 1, wherein the reservoir and the conduit are enclosed within the handheld unit.

* * * * *